United States Patent [19]

Popoff et al.

[11] Patent Number: 5,641,747

[45] Date of Patent: Jun. 24, 1997

[54] TREATMENT OF OSTEOPETROTIC DISEASES

[75] Inventors: Steven N. Popoff, Warrington, Pa.; Gary B. Schneider, Gurnee, Ill.

[73] Assignees: Temple University-Of The Commonwealth System of Higher Education, Philadelphia, Pa.; Finch University of Health Sciences/The Chicago Medical School, Chicago, Ill.

[21] Appl. No.: 280,048

[22] Filed: Jul. 25, 1994

[51] Int. Cl.$^6$ .............................. A61K 38/00; C07K 5/00; C07K 7/00; C07K 17/00

[52] U.S. Cl. ............................................. 514/12; 530/324

[58] Field of Search ................................ 514/12; 530/324

[56] References Cited

U.S. PATENT DOCUMENTS

| | | | |
|---|---|---|---|
| 5,177,001 | 1/1993 | Yamamoto | 435/68.1 |
| 5,177,002 | 1/1993 | Yamamoto | 435/68.1 |

OTHER PUBLICATIONS

Key et al., The Journal of Pediatrics, vol. 121, pp. 119–124 (1992).
Wiktor–Jedrzejczale et al., Journal of Experimental Medicine, vol. 156, pp.1516–1527 (1982).
Seifert, et al., Bone and Mineral, vol. 4, pp. 167–176 (1988).
Teitelbaum et al., Calcif. Tiss. Intl. vol. 27, pp. 255–261 (1979).
Murray et al., J. Bone Joint Surg (Br), vol. 72–B, pp. 988–992 (1990).
Popoff et al., J. Bone Min. Res. 8, Suppl. 1, S140 (Aug. 1993).
Schneider et al., FASEB J 8(4), A213 (Mar. 15, 1994).
Seifert et al., Clinical Orthopaedics 294, 23–33 (Sep. 1993).
Marks, Jr., Applied Pathology 5,: 172–183 (1987).
Marks, Jr., Clinical Orthopaedics 108, 239–263 (1984).
Chujo et al., Clin. Exp. Immunol. 76, 154–158 (1989).
Osawa et al., Biophysica et Biophysica Acta 1117, 271–278 (1992).
Mundy, J. Bone Min. Res. 8, Supp. 2: S505–510 (1993).
Yamamoto and Kumashiro, Infec. Immun. vol. 61, No. 12, 5388–5391 (1993).
Yamamoto et al., J. Immunol. vol. 151, 2794–2802, No. 5 (1993).
Homma et al., Immunology and Cell Biology 71, 249–257 (1993).
Yamamoto et al., Proc. Natl. Acad. Sci. USA 88, 8539–85432 (1991).
Yamamoto et al., J. Immunol, 147, 273–280 (1991).
Yamamoto et al., Immunology, 74, 420–424 (1991).
Baylink et al., J. Bone Min. Res. 8, Supp. 2: S565–572 (1993).
Yamamoto et al., J. Immunol. 152, 5100–5107 (May 15, 1994).
Marks, "Pathogensis of Osteopetrosis in the ia Rat: Reduced Bone Resorption Due to Reduced Osteoclast Function", Am. J. Anal. 138:165–190 (1973).
MacDonald, "Interferons" in Cytokines and Bond Metabolism, Maxine Gowen, Editor, CRC Press.
Marks et al., "Bone Cell Biology: The Reguluation of Development, Structure, and Function in the Skelton", Amer. J. Anal. 183:1–44 (1988).
Marks et al., "Osteoclast Biology in the Osteopetrotic (op) Rat", Amer. J. Anal. 186:325–334 (1989).
Popoff et al., "The Heterogeneity of the osteopetroses Reflects the Diversity of Cellular Influences During Skeletal Development", Bone 17(5):437–445 (1995).
Seifert et al., "Impaired Macrophage Migration in Incisors Absent (ia) Osteopetrotic Rats", Bone and Mineral 4:167–176 (1988).
Popoff et al., "Effect of Interferon–Gamma (IFN–γ) on Skeletal and Immune Functions in Osteopetrotic Rats", J. Bone and Mineral Research, 1995 Program & Abstracts 10(1):s504 (T600).
Popoff et al., "Differential Gene Expression in Bone From Osteopetrotic and Normal Rats", J. Bone and Mineral Research, 1995 Program & Abstracts 10(1):S504 (T601).
Teitelbaum et al., "Malignant Osteopetrosis: a Disease of Abnormal Osteoclast Proliferation", Metabolic Bone Disease & Related Research 3:99–105 (1981).
Cournot et al., "Mineral Metabolism in Infants with Malignant Osteopetrosis: Heterogeneity in Plasma 1,25–Dihydroxyvitamin D Levels and Bone Histology", J. Bone and Mineral Research 7(1):1–10 (1992).

Primary Examiner—Toni R. Scheiner
Assistant Examiner—Sheela J. Huff
Attorney, Agent, or Firm—Nixon & Vanderhye P.C.

[57] ABSTRACT

Bone resorption by osteoclast cells is promoted by activated vitamin D-binding factor, thereby providing an effective treatment for osteopetrosis. Conversely, inflammation-mediated bone loss is inhibited with antibody against the activated factor, providing a treatment for inflammation-mediated osteolytic diseases such as osteoporosis, osteoarthritis, rheumatoid arthritis and periodontal disease. The antibodies are further utilized in an antigen binding assay for diagnosing inflammation-mediated bone loss.

15 Claims, 4 Drawing Sheets

TREATMENT OF OSTEOPETROTIC DISEASES

REFERENCE TO GOVERNMENT GRANT

The invention described herein was supported in part by the National Institutes of Health, pursuant to grants R29 AR 39876 and R01 DE 06065. The United States government has certain rights in the invention.

FIELD OF THE INVENTION

The invention relates to the treatment of osteopetrosis and the treatment and diagnosis of osteolytic diseases, particularly inflammation-associated osteolytic diseases.

BACKGROUND OF THE INVENTION

The cells which make bone, osteoblasts, and those which resorb bone, osteoclasts, have very precise functions. The balance between their activities is critical to the maintenance of the skeletal system.

Osteoclasts are large, multinucleated cells. They have high capacities for the synthesis and storage of enzymes, including acid hydrolases and carbonic anhydrase isoenzyme II. Osteoclasts are derived from mononuclear cells that are the progeny of stem-cell populations located in the bone marrow, spleen, and liver. Proliferation of these stem-cell populations produces the mononuclear precursors of osteoclasts, which migrate via vascular routes to skeletal sites. These cells then differentiation and fuse with each other to form osteoclasts, or fuse with existing osteoclasts.

Activation of osteoclasts to resorb bone is generally thought to involve release of organic acids and membrane-bound packages of enzymes onto the bone surface. This requires elaboration next to the bone surface of a specialized region of the plasma membrane, the ruffled border. In this region the osteoclast's prepackaged, membrane-bound enzymes can fuse with the plasma membrane and be released onto the bone surface in a confined extracellular space. Degradation of the inorganic and organic tissue occurs in this area. The products of resorption are then taken up via endocytosis for additional intracellular processing within cytoplasmic vacuoles.

Osteopetrosis is an inherited defect characterized by a failure of normal bone resorption (modeling) and, as a result, excessive bone accumulation throughout the skeleton. Osteopetrosis occurs in a number of species, including man. The disease represents a heterogeneous group of bone disorders both in animal species demonstrating these defects and in the infantile malignant forms of osteopetrosis. The skeletal sclerosis and reduced bone marrow resorption in certain animal species have been shown to be due to defective osteoclasts. The skeletal abnormalities associated with osteopetrosis lead to a number of problems, including anemia, infection, optic atrophy, deafness and various neuropathies. The life expectancy of osteopetrotic patients is less than ten years.

Presently available forms of treatment for osteopetrotic children include bone marrow transplantation and interferon-gamma therapy. Bone marrow transplantation is not available to most osteopetrotic children and not all children who receive bone marrow transplants respond favorably. Interferon-gamma therapy has demonstrated moderate success in stimulating osteoclast function (Key et al., *J. Pediatr.* 121, 119–24, 1992) but requires high doses and extensive clinical monitoring to avoid the potential toxic effects associated with this cytokine.

The study of osteopetrosis has been facilitated by the existence of a number of osteopetrotic animal mutations. For a discussion of such mutations, see Marks, *Clinical Orthopedics*, 180, 239–263, 1984. The "incisors-absent" (ia) (Greep, *J. Hered.* 32:397, 1941) and osteopetrotic (op) (Moutier et l., *Animal* 6:87, 1973) rat mutations, as well as certain other animal congenital osteopetrotic mutations, have been shown to respond to spleen cell or bone marrow transplantation (Marks, *Am. J. Anat.* 146:331, 1976; Milhaud et al., *C.R. Acad. Sci. Paris* 280:2485, 1975), thereby paving the way for the first successful reported treatment of congenital human osteopetrosis by Ballet et al., *Lancet* 2:1137, 1977. Hence these mutations provide an acceptable corollary to human osteopetrosis.

Inflammation-mediated bone loss occurs in numerous diseases such as osteoporosis, periodontal disease, osteoarthritis, and rheumatoid arthritis. Osteoporosis is a major skeletal disease characterized by low bone mass, architectural deterioration, and an increased risk of fracture. It is implicated in more than 1.5 million fractures per year in the United States. There is evidence of significant mortality and morbidity associated with osteoporosis. The cost of osteoporotic fractures in the United States is estimated at $7–10 billion annually.

As peak bone mass is attained, usually between the ages of 35 and 40 in humans, a slight imbalance occurs between the processes of bone formation by osteoblasts and bone resorption by osteoclasts. The amount of bone resorbed by osteoclasts is not entirely replaced by osteoblasts. The speed of bone remodeling (bone turnover) increases after menopause. The outcome is accelerated loss of bone and a negative calcium balance.

Bone loss in the oral cavity is likewise a significant problem in the United States. Interdisciplinary attention has recently focused on possible relationship between osteoporosis and oral bone loss (*Proceedings of the Workshop on Oral Bone Loss and Osteoporosis*, Leesburg, Va., Aug. 26–28, 1992, in *J. Bone Miner. Res.* 8, Supplement 2, 1993).

Periodontitis is characterized by loss of bone and soft tissue attachment. The response to the formation of microbial plaque is an inflammation of the gingiva and the resulting breakdown of tissues. This causes the formation of an opening along the tooth surface known as the "periodontal pocket". The bone remodeling that occurs in periodontal disease is typically localized to the alveolar bone. The mechanism of alveolar bone loss in periodontal disease is believed to be the same basic mechanism as is responsible for bone loss associated with other types of inflammatory conditions. It has been presumed that accumulations of chronic inflammatory cells generate inflammatory cytokines and local mediators that are responsible for enhanced osteoclastic resorption and inhibition of repair or new bone formation at the sites of resorption. For instance, inflammatory mediators, such as prostaglandins (Offenbacher et al., *J. Periodont. Res.* 21, 101–112, 1986) have been associated with active progression of periodontitis. IL-1, another mediator of inflammation, has been found in gingival crevicular fluid during inflammation (Charon et al., *Infect. Immun.* 38, 1190–95, 1982).

Inflammation-mediated bone loss is a problem of major clinical and economic significance. Studies attempting to identify the factor(s) which mediate bone loss have implicated various immune cell products, i.e. cytokines and growth factors. For a recent short review see Mundy, *J. Bone Miner. Res.* 8, Supplement 2, S505–S510, 1993. It has been suggested that the major mediators likely involved include interleukin 1, tumor necrosis factor-α, lymphotoxin, interleukin 6, prostaglandins of the E series, leukotrienes, lipopolysaccharide, transforming growth factor-β, and the colony-stimulating factors. But no studies have provided conclusive evidence of cytokines' pathogenic role in bone degradation. Some studies have yielded conflicting data. The production of a particular cytokine may be elevated in some patients but not in others, yet all have the same disease and demonstrate similar amounts of bone loss. Based on these studies, the treatment strategies designed to help prevent the bone loss associated with inflammation have either been ineffective or have shown limited therapeutic efficacy in a subset of patients with a specific disease.

SUMMARY OF THE INVENTION

A method of promoting osteoclast bone resorption and treating osteopetrosis is provided, comprising administering to an individual in need of such treatment an effective amount of activated vitamin D binding factor. The factor may comprise human or non-human mammalian activated vitamin D binding factor.

According to another embodiment of the invention, a method of inhibiting inflammation-mediated bone loss and inflammation-mediated osteolytic disease is provided comprising administering to an individual in need of such treatment an effective amount of an antibody capable of inhibiting activated vitamin D binding factor. The antibody is preferably a monoclonal antibody. The antibody is more preferably a chimeric monoclonal antibody, such as a human chimeric antibody. Inhibition of inflammation-mediated bone loss provides a treatment for inflammation-mediated osteolytic diseases such as osteoarthritis, periodontal disease, rheumatoid arthritis and osteoporosis.

The invention also provides monoclonal antibody which specifically binds to an antigenic determinant of activated vitamin D binding protein and which inhibits the bone resorption-stimulating activity of activated vitamin D binding protein.

The invention further provides a method for diagnosing inflammation-mediated bone loss. A bodily sample from an individual suspected of affliction with inflammation-mediated bone loss is contacted with an antibody, preferably a monoclonal antibody, which specifically binds to an antigen determinant of activated vitamin D binding protein, and which does not recognize unactivated DBP. The sample is then assayed for binding of activated vitamin D binding protein by the antibody.

By "vitamin D-binding protein" or "DBP" as used herein means the genetically polymorphic glycoprotein vitamin D-binding protein, also known as "group specific component" ("Gc") in humans, including all genetic variations thereof. The singular expression "DBP" is thus understood to encompass all such variants, unless stated otherwise.

By "activated vitamin D-binding protein", "activated DBP" or "DBP-MAF" is meant DBP which has been converted to a macrophage activating factor by the action of certain glycosidases. By "GcMAF" is meant the human form of activated DBP.

By "macrophage activation" is meant the stimulation of macrophages to an increased level of phagocytic activity.

By "inflammation-mediated bone loss" is meant bone loss in an animal or human associated with activation of the inflammatory cascade, as characterized by the production of DBP-MAF.

By "inflammation-mediated osteolytic disease" is meant a disease characterized by an inflammation-mediated bone loss.

By "antibody" is meant not only intact antigen-binding immunoglobulin molecules, but also antigen-binding fragments thereof such as Fab, Fab' and F(ab')$_2$ fragments, or any other fragment retaining the essential function of binding antigen.

By "chimeric antibody" is meant an antibody comprising a variable region and a constant region derived from different species.

By "humanized chimeric antibody" is meant a chimeric antibody in which at least the constant region is human-derived.

DETAILED DESCRIPTION OF THE INVENTION

Figure 1:
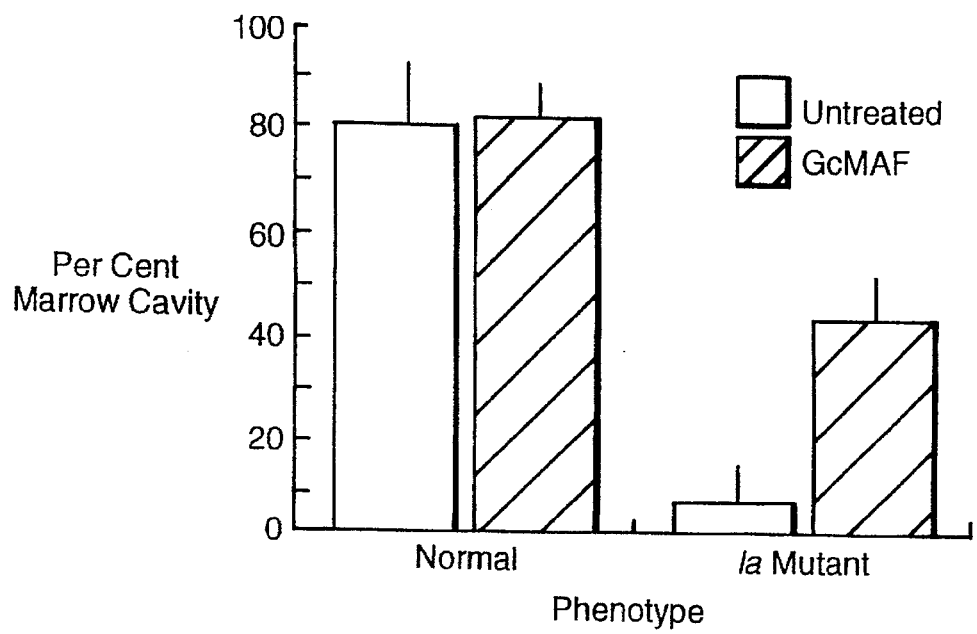
FIG. 1 is a graph of tibial marrow cavity size of normal and ia mutant rats in response to treatment with GcMAF. Bars represent the mean±SEM.

We have found that DBP, once converted to its potent macrophage activator form, has the heretofore unknown ability to activate osteoclast function (bone resorption). It appears that activated DBP is at least 1,000 times more potent than other stimulators of bone resorption. Thus, its ability to activate osteoclasts and remove excess bone in osteopetrotic individuals may be achieved without the toxic side-effects of other stimulatory agents. Activated DBP is effective at nanogram levels in stimulating bone resorption in vitro, as compared to the microgram levels required for γ-interferon. Moreover, the discovery of activated DBP's key role in mediating bone loss provides a target for therapeutic intervention in the treatment of osteolytic disorders. Antibodies, preferably monoclonal antibodies, may be used to block the activity of DBP-MAF to prevent bone loss in inflammation-mediated osteolytic disorders, independent of the location of the inflammatory site. For example, antibody to DBP-MAF may be administered to prevent alveolar bone loss associated with periodontal disease, as well as loss from vertebrae or long bones in osteoarthritis.

Vitamin D-binding protein is an evolutionary conserved but genetically polymorphic plasma glycoprotein present in the $\alpha_2$-globulin fraction of sera. DBP from animals serologically cross-reacts with human DBP. DBP normally constitutes about 0.5% of the plasma proteins in animals. The plasma concentration is generally about 260 µg/ml.

Native DBP carries a single oligosaccharide moiety containing galactose and sialic acid as dibranched termini at N-acetylgalactosamine. Portions of the oligosaccharide are readily removable by treatment with readily available glycosidases. These glycosidases are equivalent to the functions of B and T cells upon DBP.

Polymorphism in DBP is expressed, both in the oligosaccharide moiety and in the polypeptide portion of the glycoprotein. Polymorphism of the human DBP, known as "group specific component" or "Gc protein", is demonstrable by gel electrophoretic analysis, which reveals two major phenotypes: Gc1 and Gc2. The DBPgs and DBPgm phenotypes (Gc1 in humans) differs from the DBPg phenotype (Gc2 in humans) by four amino acids at positions 152, 311, 416 and 420. The entire nucleotide coding sequences of the Gc1 and Gc2 genes, and the predicted amino acid sequences, have been reported in the literature (Cooke, et al., *J. Clin. Invest.* 76:2420, 1985; Yang et al., *Proc. Natl. Acad. Sci. USA* 82:7994, 1985). Gc1 is further divided into Gc1f and Gc1s subtypes which migrate electrophoretically as two bands, "fast" and "slow", (Svasti et al., *Biochem.* 18:1611, 1979).

According to U.S. Pat. Nos. 5,177,001 and 5,177,002 to Nobuto Yamamoto, the entire disclosures of which are incorporated herein by reference, DBP phenotypes and subtypes are characterized as glycoproteins having the following oligosaccharide structures linked to an amino acid residue of the protein portion of the molecule:

| DBP Type | Oligosaccharide | Representative Species |
|---|---|---|
| DBPgs | Gal—GalNAc—<br>\|<br>NeuNAc | human (Gc1f, Gc1s*),<br>monkey, bovine,<br>sheep,<br>goat, pig, horse |
| DBPgm | Gal—GalNAc—<br>\|<br>αMan | human (Gc1s, Gc1f*),<br>bovine |
| DPBg | Gal—GalNAc— | human (Gc2), dog,<br>cat, rat, mouse |

As further described by Yamamoto, DBP is activated to DBP-MAF with (i) β-galactosidase, or (ii) β-galactosidase in combination with sialidase, α-mannosidase, or a mixture thereof. DBPg treated with β-galactosidase alone results in removal of galactose and the formation of activated DBP. Conversion of DBPgs to the activated form requires incubation with the combination of β-galactosidase and sialidase. DBPgm conversion requires β-galactosidase and α-mannosidase. Activated DBP thus comprises a protein having substantially the amino acid sequence of DBP and a terminal N-acetylgalactosamine group. The glycosylation is in DBP domain III, in the vicinity of amino acid 420. Domain III comprises a region of DBP from about Ser-373 to the COOH-terminus at Ser-460. According to Yamamoto, the glycosylation occurs at Thr(418) in human DBPg (Gc2), or Thr(418) (or Thr(420)) in DBPgs/gm, or Ser(418) in those species of DBPg, such as rat and mouse DBPg, which contain serine at position 418 in lieu of threonine.

DBP for conversion to DBP-MAF may be obtained by 25-hydroxyvitamin $D_3$-SEPHAROSE® (agarose beads) affinity chromatography of blood according to the procedure of Link et al., *Anal. Biochem.* 157, 262 (1986). DBP may also be purified by actin-agarose affinity chromatography according to the procedure of Haddad et al., *Biochem. J.* 218, 805 (1984), which takes advantage of the binding specificity of DBP for actin.

DBP is then converted to DBP-MAF by appropriate in vitro glycosidase treatment. As described by Yamamoto, about 0.1 units (1 unit being the amount of enzyme which catalyzes 1 µmole of substrate in 1 minute) of each enzyme per 1 µg of DBP in phosphate buffer is sufficient for this purpose. The temperature may vary from 25° C. to 37° C., with about 37° C. being preferred. A reaction time of about 30 minutes at 37° C. is generally sufficient to obtain complete conversion of DBP to DBP-MAF. Preferably, all enzymes are most advantageously contained in the solid phase. For example, the enzymes may be fixed to agarose beads with a suitable coupling agent such as cyanogen bromide. Methods for attaching enzymes to solid supports are known to those skilled in the art.

For further discussions regarding the conversion of DBP to the potent macrophage activator form see Yamamoto and Homma, *Proc. Natl. Acad. Sci. USA* 88, 8539–8543, 1991; Homma et al., *Immunol. Cell Biol.*, 249–257, 1993; Yamamoto and Kumashiro, *J. Immunol.* 151, 2794–2802, 1993; and Yamamotb U.S. Pat. Nos. 5,177,001 and 5,177,002.

Animal mutations are recognized as invaluable tools for probing the pathogenesis and treatment of osteopetrosis; information obtained from studies of these mutations has been used clinically for the treatment of humans with osteopetrosis. See the following reviews of these mutations as models for osteopetrosis: Siefert et al., *Clinical Orthopedics* 294, 23–33, 1993; Marks, *Appl. Pathol.* 5, 172–183, 1987; and Marks, *Clin. Orthop.* 180, 239–263, 1984.

All of the commonly studied animal mutations are inherited as an autosomal recessive trait. The skeletal manifestations of these animal osteopetroses are similar. Marrow cavity formation is either delayed or more commonly absent, thereby producing the pathognomic radiographic appearance of homogeneously dense bones. The skeletal cells and matrices vary significantly among the various mutations. Juvenile osteopetrosis in humans is also inherited as a recessive trait. It is usually lethal in the first decade of life.

The potent stimulatory effect of DBP-MAF on bone resorption may be demonstrated with resort to two such animal models of osteopetrosis. The osteopetrotic (op) rat is a lethal mutation in which osteoclast and macrophage activation appear to be defective. Osteoclasts are significantly reduced in number and are defective in their ability to resorb bone. The animals demonstrate generalized sclerotic bone due to reduced bone resorption. The sclerosis is severe and persists with age.

Inflamed tissues produce lysophospholipids, such as lysophosphatidylcholine (lyso-Pc) which activates macrophages to phagocytose target antigens or cells via the Fc receptor and to generate superoxide. Previous studies have shown that inflammation-primed macrophage activation involves a sequence of events in which DBP is converted by the sequential actions of lyso-Pc-inducible β-galactosidase and sialidase isoenzymes associated with B and T cell membranes, respectively (Yamamoto and Homma, *Proc. Natl. Acad. Sci. USA* 88, 8539–8543, 1991).

We determined that in vivo treatment with lyso-Pc caused a dramatic increase in macrophage number and superoxide production in normal rats but failed to do so in op rats. We performed a series of in vitro assays to determine the nature of the defect in op macrophage activation. These assays revealed that mutant op B cells were deficient in lyso-Pc-inducible β-galactosidase activity, an isoenzyme necessary for the conversion of DBP to DBP-MAF. Other studies demonstrated that mutant serum was not deficient in DBP and that op macrophages could be activated when treated with exogenously generated DBP-MAF. Further, newborn op rats treated with DBP-MAF generated ex vivo using commercially available glycosidases displayed an increased number of osteoclasts. The majority of the osteoclasts exhibited normal morphology. There was also reduced bone volume in the treated op animals, and an increasing cellularity of the marrow spaces.

Another osteopetrotic rat mutation, the "incisors absent" (ia) mutation, is also characterized by generalized sclerotic bone. The skeletal sclerosis in ia rats is not as severe as in op rats, but like op, it persists with age. The ia rats have elevated numbers of osteoclasts, but the cells are morphologically abnormal. They lack a ruffled border. As in the case of the op mutation, administration of lyso-Pc to ia rats failed to activate macrophages. However, subsequent examination of the individual steps in the activation cascade revealed that unlike op rats, ia rats were not deficient in lyso-Pc-inducible β-galactosidase associated with B cell membranes. Rather, ia mutants demonstrated a defect in serum DBP itself. Treatment of ia mutant rats with exogenously generated DBP-MAF resulted in correction of skeletal sclerosis, as in the DBP-MAF-treated op animals. Marrow cavity size was significantly enlarged and the majority of the osteoclasts appeared normal.

Transplantation of hematopoietic stem cells from normal littermates to osteopetrotic mutant siblings has been shown to cure skeletal sclerosis, including skeletal sclerosis in ia and op rats. These animal studies were directly responsible for the first clinical treatments of children with osteopetrosis. Hence, the ia and op mutations in rats have been established as valid animal models for treatment of human disease. Moreover, the ia mutant rats in particular have been recognized as an animal model for the treatment of otosclerosis (more accurately otospongiosis), a hearing disorder characterized by formation of otospongiotic foci in the labyrinthine capsule of the ear (Kaniff et al., *Otolaryngol.—Head & Neck* 103(3), 406–412, 1990).

DBP-MAF may be administered either locally or systemically to treat osteopetrotic disorders in mammals, inclusive of humans. Candidates for human treatment comprise any osteopetrotic individuals, particularly children with congenital osteopetrosis. For systemic delivery, DBF-MAF may be administered by any convenient route which will result in delivery to the circulation of an amount of the factor sufficient to induce substantial bone resorption. Any route acceptable for the delivery of proteinaceous pharmaceuticals may be employed. Parenteral administration is preferred. For example, DBF-MAF may be given by subcutaneous, intravenous, intraarterial, intraperitoneal or intramuscular injection. For local administration to a site of bone accumulation, DBF-MAF may be given by direct local injection, by continuous infusion via infuser pumps, by implantation of controlled release devices, and the like.

To minimize any possible immunologic reaction from administration of DBF-MAF, it is preferred that the patient would receive only DBF-MAF derived from the blood of the same species. Similarly, the risk of immunologic reaction in individuals would be minimized by administering only the same variant of DBF-MAF, in situations wherein there is intraspecies DBP polymorphism. For example, a Gc1 human patient would receive Gc1MAF, that is, GcMAF generated from enzymatic cleavage of group specific component type Gc1. However, the risk of immune reaction from cross-species administration of DBP-MAF is believed minimal due to the high level of evolutionary conservation in that molecule. As demonstrated hereinafter, ia and op rats tolerated treatment with human DBP-MAF (GcMAF).

DBF-MAF may be taken up in pharmaceutically acceptable carriers, particularly those carriers suitable for delivery of proteinaceous pharmaceuticals. The factor is soluble in water or saline solution. Thus, the preferred formulation for veterinary pharmacological use comprises a saline solution of the agent. The formulation may optionally contain other agents, such as agents to maintain osmotic balance. For example, a typical carrier for injection may comprise an aqueous solution of 0.9% NaCl or phosphate buffered saline (a 0.9% NaCl aqueous solution containing 0.01M sodium phosphate, ≈pH 7.0). The amount of active compound in the formulation is such that a suitable dosage will be obtained.

The dosage is generally similar to the dosage recommended for induction of macrophage activation. See U.S. Pat. Nos. 5,177,001 and 5,177,002. The amount of DBP-MAF administered depends on a variety of factors, including the potency of the preparation, the size and weight of the subject, the extent of the affliction, and the like. A dosage of as little as 1 nanogram per kg has been shown to result in significant skeletal improvement. A representative treatment regimen may comprise, for example, from about 1 ng to about 10 μg of DBF-MAF administered parenterally on an intermittent basis, e.g. every fourth day, preferably from about 10 ng to about 1 μg. It is contemplated that treatment would extend indefinitely, as the underlying disease lesion is genetically determined.

The results of DBP-MAF therapy can be noninvasively monitored through visualization of the marrow cavity using skeletal densitometry or skeletal X-ray. These procedures are capable of indicating a reduction in bone mass. Invasive monitoring of therapy may be carried out by periodic bone biopsy, such as from the iliac crest of the pelvis bone. The bone is fixed and the tissue prepared in the same manner as in the post mortem bone biopsies of DBP-MAF-treated ia and op rats described in the hereinafter Examples.

Osteopetrotic children typically also display immune disorders. Immune function may be monitored over the course of DBP-MAF therapy. For example, the levels and function of neutrophils, macrophages and natural killer cells may be assessed by conventional procedures. One can also monitor hematology, as well as visual and auditory acuity as indicators of neurological development. Osteopetrotic children typically display complications associated with neurological development.

The macrophage activating activity of DBP-MAF, and its osteoclast-stimulating activity as well, is a function of DBP-MAF domain III, particularly the site of N-glycosylation. One of the amino acids between positions 416 to 420 represents the site of N-glycosylation. Antibodies may be prepared against the epitope or epitopes of the glycosylation site by conventional immunologic techniques. Such antibodies, which comprise inhibitors of DBP-MAF, may be used to block the resorptive effect of DBP-MAF at sites where excessive bone loss is associated with inflammation. These blocking antibodies may be used to treat inflammation-mediated osteolytic disorders such as rheumatoid arthritis, osteoarthritis, periodontal disease, and osteoporosis.

Polyclonal antibodies useful in the invention are obtained by well-known techniques. These include stimulating an immune response against DBP-MAF in a suitable host. Serum is taken from the host and then subjected to affinity purification to isolate polyclonal antibodies against the immunogen. Monoclonal antibodies are preferred.

An anti-DBP-MAF monoclonal antibody, or mixture of such antibodies, is administered either locally or systemically to treat inflammation-mediated bone loss and inflammation-mediated osteolytic disease in mammals, inclusive of humans. Candidates for human treatment comprise any osteolytic individual wherein the disorder has an inflammation-mediated component, i.e., the bone loss arises from the activation of the inflammatory cascade, and the attendant production of DBP-MAF. Osteolytic disorders having an inflammation-mediated component are distinguished from noninflammatory bone loss conditions such as disuse osteoporosis, and osteoblast dysfunction leading to an imbalance in bone remodeling toward net bone loss. The latter has been recently associated with interleukin 4 overproduction in a transgenic mouse model (Lewis et al., *Proc. Natl. Acad. Sci. U.S.A.* 90, 11618–11622, 1993). Whether a particular occurence of bone loss is associated with inflammation can be readily determined by assaying the appropriate specimen (e.g., blood plasma, sinovial fluid, or gingival fluid) with anti-DBP-MAF antibodies in the diagnostic assay described elsewhere herein.

For systemic delivery, anti-DBP-MAF antibody may be administered by any convenient route which will result in delivery to the circulation of an amount of antibody sufficient to inhibit bone resorption. Any route acceptable for the delivery of proteinaceous pharmaceuticals may be employed. Parenteral administration is preferred. For example, anti-DBP-MAF antibodies may be given by subcutaneous, intravenous, intraarterial, intraperitoneal or intramuscular injection. For local administration to a site of bone loss, anti-DBP-MAF antibody may be given by direct local injection, by continuous infusion via infuser pumps, by implantation of controlled release device, and the like. For treatment of osteoarthritis, rheumatoid arthritis and periodontal disease, local administration of anti-DBP-MAF antibodies is preferred. For treatment of periodontal disease in particular, the antibody may be advantageously incorporated into a controlled release dosage form, suitable for insertion into the periodontal pocket. Such dosage forms are known to those skilled in the art. See, for example, U.S. Pat. No. 5,143,934.

Anti-DBP-MAF antibody may be taken up in the same type of pharmaceutically acceptable carriers as may be used for delivery of DBP-MAF. The dosage of anti-DBP-MAF administered depends on the relative affinity of the antibody for DBP-MAF, the stability of the antibody, the size and weight of the subject, the extent of the bone loss, and the like. A dosage of from about 1 ng to about 10 mg of anti-DBP-MAF antibody may be given as needed to maintain this balance. It is contemplated that treatment would be given intermittently whenever the balance of bone remodeling in the patient has been observed to shift to net resorption. The latter condition will be manifested by measurable bone loss. The need for treatment would also be apparent from an increase in the amount of DBP-MAF, either systemically or at the local bone loss site. The level of DBP-MAF in bodily specimens of interest may be determined according to the assay described later herein.

The results of the anti-DBP-MAF therapy may be monitored noninvasively via bone densitometry. This technique depends on the measurement of the relative attenuation of photons by the mineral component of bone and any other material in the path of a photon beam. The dual photon absorptiometry variation of bone marrow densitometry is preferred. For a discussion of current methodologies of bone imaging, see Cann., *J. Bone Min. Res.* 8, Supp. 2, S535–S542, 1993.

The results of anti-DBP-MAF therapy may be monitored by assaying for the presence of specific break-down products generated as a consequence of bone resorption. For example, the level of N-telopeptides of type I collagen may be assayed in urine using an enzyme-linked immunosorbent assay relying on a monoclonal antibody which recognizes such peptides. See Hanson et al., *J. Bone Min. Res.* 7, 1251–1258 (1992). Kits for measuring N-telopeptides in urine are commercially available (OSTEOMARK, Ostex International, Inc., Seattle, Wash.).

Anti-DBF-MAF monoclonal antibodies are prepared by immunizing an appropriate host with DBF-MAF. The immunogen may be isolated as described above. Polyclonal and monoclonal antibodies against human DBP, i.e., Gc, have been prepared in animals. See Chujo et al., *Clin. Exp. Immunol.* 76, 154–158, 1989; Osawa et al., *Biochim. Biophys. Acta* 1117, 271–278, 1992.

According to one method of antibody preparation, mice are immunized with DBF-MAF. BALB/cAnSkh mice are preferred, although other strains may be used. The immunization schedule and concentration of immunogen administered should be such so as to produce useful quantities of suitably primed splenocytes.

Upon completion of the immunization regimen, more fully described below, the mice are sacrificed and their spleens removed. A suspension of splenocytes in a suitable medium is prepared. Approximately 2.5–5 ml of medium per spleen is sufficient. The protocols for in vitro cell suspension are well established.

The spleen cells are fused with mouse myeloma cells by means of a fusion promoter. The preferred fusion promoter is polyethylene glycol ("PEG"), molecular weight 1,300–1,600 kDa. Other known fusion promoters may be used. The mouse myeloma cell line is preferably one of the "drug-resistant" types, to enable selection of hybrids. The most frequently used class of myelomas are the 8-azaguanine-resistant cell lines, which are widely known and available. These cell lines lack the enzyme hypoxanthine guanine phosphoribosyl transferase and therefore do not survive in "HAT" (hypoxanthine-aminopterinthymidine) medium. The use of myeloma cells with different genetic deficiencies (e.g., other enzyme deficiencies, drug sensitivities, etc.) that can be selected against in a medium supporting the growth of genotypically competent hybrids is also possible. Additionally, it is suggested that the myeloma cell line should not itself produce any antibody, although in some circumstances secreting myeloma cell lines may be used.

While the preferred fusion promoter is PEG of average molecular weight 1,300–1,600 kDa (available from ATCC), other known fusion promoters may be used.

Fusion of cells may be carried out in an adherent monolayer, such as according to the method described by T. J. McKearn, "Fusion of Cells in an Adherent Monolayer" in *Monoclonal Antibodies: Hybridomas: A New Dimension In Biological Analysis*, (Kennett, R. H., McKearn, T. J., and Bechtol, K. B., eds., Plenum Press, New York and London, 10368–369, 1980). Other fusion techniques may be employed. A cell ratio of 2–5:1 spleen cells per myeloma cell may be used. This ratio may be varied depending on the source of spleen or myeloma cells.

A mixture of unfused myeloma cells, unfused spleen cells and fused cells are distributed for culturing in separate compartments (e.g., the wells of microtiter plates) in a selective medium in which the unfused myeloma cells will not survive. Distribution of the cells may be by resuspension in a volume of diluent which is statistically calculated to isolate a desired number of cells per compartment. See, McKearn, T. J., "Cloning of Hybridoma Cell Lines by Limiting Dilution in Fluid Phase" in *Monoclonal Antibodies*, p. 374.

When HAT is used as the medium, unfused 8-azaguanine-resistant myeloma cells will not grow. Unfused spleen cells will normally die after a few days, since they are non-malignant. Culturing proceeds for a time sufficient to allow their death. Fused cells continue to reproduce and grow in the selective medium.

The supernatant in each container or compartment having hybrid cell growth is screened and evaluated for the presence of antibody to DBF-MAF. Any suitable antibody-binding detection method may be used, e.g., ELISA, radioimmunoassay, etc. The supernatants are further screened for their ability to inhibit bone resorption by osteoclasts. Alternatively, functional assay of anti-DBP-MAF clones may be postponed until after antibody isolation, as described below.

After selection and cloning, the desired monoclonal antibody to the DBF-MAF may be produced by in vitro culturing of the hybridomas or by in vivo peritoneal exudate induction in mice. The first method will yield monoclonal antibody of higher purity. The antibody is recovered from the supernatant essentially free of undesired immunoglobulin. Antibody concentrations of 25–50 micrograms/ml are possible by this method. In growth media containing serum (such as fetal calf serum) a small amount of other immunoglobulin is present.

Where concentrations of antibody larger than those obtained by in vitro culturing of hybridomas are required, the subject hybridomas may be injected into the peritoneal cavity of syngeneic or semisyngeneic mice. After a suitable period of incubation, the hybridomas cause formation of antibody-secreting tumors, which will produce 4–10 mg of antibody per ml of peritoneal exudate of the injected mouse. Since mice have normal antibodies in their blood and ascites, a contamination of about 5% from the host mouse is inevitable. Purification of ascites monoclonal antibody may remove these contaminants. The resultant antibody is of high titer, being active at dilutions of 1:300,000 or higher.

Anti-DBF-MAF antibodies may be screened for ability to inhibit osteoclast bone resorption by any of the known assays for monitoring osteoclast function, such as any of the assays described in the hereinafter Examples. Screening is most advantageously carried out by culturing primary bone cells, such as rat bone cells, with candidate inhibitor antibody on synthetic or natural bone substrates. Where newborn animals are used as bone cell donors, the harvested population is rich in osteoclasts. The culture condition for these cells are selected so as to maintain osteoclast cells on the substrate, under conditions allowing bone resorptive activity by osteoclast cells. Osteoclast function, that is, bone resorption, is determined by the appearance of microscopic lacunae on the film, similar to the resorptive lacunae formed in normal bone tissue. Imaging of the resulting lacunae following culture provides a simple quantitative method for rapidly screening antibodies for ability to inhibit osteoclast bone resorption.

The substrate for culturing of osteoclasts may comprise a synthetic or natural substrate. For example, sub-micron calcium phosphate ceramic thin films may be formed by vertically dipping transparent quartz plates in a particulate sol-gel suspension. Preparation of these films, and their use as substrates in assays of osteoclast activity, is described by Davies et al., *Cells and Materials* 3 (30), 245–256, 1993. The same films are now commercially available from Millenium Biologix Inc., Kingston, Ontario, under the trademark OSTEOLOGIC. Alternatively, the substrate may comprise a natural substrate such as bone or dentine. Methods for determining osteoclast activity using such substrates are known. See, for example, Chambers et al., *J. Cell Sci.* 66, 383–399, 1984 (bone); Boyde et al., *Br. Dent. J.* 156, 216–220, 1984 (dentine).

Bone resorption may be assessed using a variety of techniques. The number of resorption pits on the substrate may be determined by counting under a light microscope (Murrills and Dempster, *Bone*, 11, 333–344 (1990)). The area occupied by resorption pits can also be quantitated by image analysis (Davis et al., *Cells and Materials* 3, 245–256 (1993)). Alternatively, the samples may be processed for scanning election microscopy (SEM) to quantirate bone resorption (Chambers et al., *J. Cell Sci.* 70, 61–71 (1984); Boyde et al., *Scanning Electron Microscopy III*, 1239–1271 (1985)). Area or volumetric measurements of pit formation can be assessed by SEM. All of these methods are well known to those skilled in the art.

Preferably, antibodies are selected which are specific for DBF-MAF and do not cross-react with unactivated DBP. This may be achieved by the simple expedient of counter-screening anti-DBP-MAF positive clones with DBP. Clones producing antibody binding unactivated DBP are eliminated. The remaining clones provide monoclonal antibody which is specific for an antigenic determinant present on DBF-MAF but absent from DBP. That is, the clones provide monoclonal antibody specific for a determinant comprising the terminal N-acetylgalactosamine group of DBF-MAF, a determinant antigenically distinct from determinants formed by the Gal-Gal-(NeuNAc/αMan)NAc and Gal-GalNAc oligosaccharide moieties of unactivated DBP. Thus, the monoclonal antibodies are directed against an epitope of DBP-MAF responsible for stimulating osteoclast bone resorption.

The anti-DBP-MAF monoclonal antibodies may be advantageously cleaved by proteolytic enzymes to generate fragments retaining the antigen-binding site. For example, proteolytic treatment of IgG antibodies with papain at neutral pH generates two identical so-called "Fab" fragments, each containing one intact light chain disulfide-bonded to a fragment of the heavy chain (Fd). Each Fab fragment contains one antigen-combining site. The remaining portion of the molecule is a dimer known as "Fc". Similarly, pepsin cleavage at pH 4 results in the so-called F(ab')$_2$ fragment.

Methods for preparation of such fragments are known to those skilled in the art. See, Goding, *Monoclonal Antibodies Principles and Practice*, Academic Press (1983), p. 119–123. Fragments of the anti-DBF-MAF monoclonal antibodies containing the antigen binding site, such as Fab and F(ab')$_2$ fragments, may be preferred in therapeutic applications, owing to their reduced immunogenicity. Such fragments are less immunogenic than the intact antibody, which contains the immunogenic Fc portion.

The effects of sensitization in the therapeutic use of animal origin monoclonal antibodies in the treatment of human disease may be diminished by employing a hybrid molecule generated from the same Fab fragment, but a different Fc fragment, than contained in Mabs previously administered to the same subject. It is contemplated that such hybrid molecules formed from the monoclonal antibodies of the invention may be used in therapy. The effects of sensitization are further diminished by preparing animal/human chimeric antibodies, e.g., mouse/human chimeric antibodies, or humanized (i.e. CDR-grafted) antibodies. Such monoclonal antibodies comprise a variable region, i.e., antigen binding region, and a constant region derived from different species.

Chimeric animal-human monoclonal anti-DBP-MAF antibodies may be prepared by conventional recombinant DNA and gene transfection techniques well known in the art. The variable region genes of a mouse antibody-producing myeloma cell line of known antigen-binding specificity are joined with human immunoglobulin constant region genes. When such gene constructs are transfected into mouse myeloma cells, antibodies are produced which are largely human but contain antigen-binding specificities generated in mice. As demonstrated by Morrison et al., *Proc. Natl. Acad. Sci. USA* 81, 6851–6855, 1984, both chimeric heavy chain V region exon ($V_H$)-human heavy chain C region genes and chimeric mouse light chain V region exon ($V_K$)-human K light chain gene constructs may be expressed when transfected into mouse myeloma cell lines. When both chimeric heavy and light chain genes are transfected into the same myeloma cell, an intact $H_2L_2$ chimeric antibody is produced. The methodology for producing such chimeric antibodies by combining genomic clones of V and C region genes is described in the above-mentioned paper of Morrison et al., and by Boulianne et al., *Nature* 312, 642–646, 1984. Also see Tan et al., *J. Immunol.* 135, 3564–3567, 1985 for a description of high level expression from a human heavy chain promotor of a human-mouse chimeric K chain after transfection of mouse myeloma cells. As an alternative to combining genomic DNA, cDNA clones of the relevant V and C regions may be combined for production of chimeric antibodies, as described by Whitte et al., *Protein Eng.* 1, 499–505, 1987 and Liu et al., *Proc. Natl. Acad. Sci. USA* 84, 3439–3443, 1987.

For examples of the preparation of chimeric antibodies, see the following U.S. Patents: U.S. Pat. nos. 5,292,867; 5,091,313; 5,204,244; 5,202,238; and 5,169,939. The entire disclosures of these patents, and the publications mentioned in the preceding paragraph, are incorporated herein by reference. Any of these recombinant techniques are available for production of rodent/human chimeric anti-DBP-MAF monoclonal antibodies.

To further reduce the immunogenicity of murine antibodies, "humanized" antibodies have been constructed in which only the minimum necessary parts of the mouse antibody, the complementarity-determining regions (CDRs), are combined with human V region frameworks and human C regions (Jones et al., *Nature* 321, 522–525, 1986; Verhoeyen et al., *Science* 239, 1534–1536, 1988; Reichmann et al., 322, 323–327, 1988; Hale et al., *Lancet* 2, 1394–1399, 1988; Queen et al., *Proc. Natl. Acad. Sci. USA* 86, 10029–10033, 1989). The entire disclosures of the aforementioned papers are incorporated herein by reference. This technique results in the reduction of the xenogeneic elements in the humanized antibody to a minimum. Rodent antigen binding sites are built directly into human antibodies by transplanting only the antigen binding site, rather than the entire variable domain, from a rodent antibody. This technique is available for production of chimeric rodent/human anti-DBP-MAF antibodies of reduced human immunogeneicity.

Anti-DBP-MAF monoclonal antibodies which fail to recognize unactivated DBP are used according to the present invention in a method for measuring the level of DBP-MAF in specimens of interest. The sample is contacted with anti-DBP-MAF-specific monoclonal antibody. The sample is then assayed for binding of DBP-MAF to the antibody by standard immunoassay.

Anti-DBP-MAF antibodies may be used to measure local levels of DBP-MAF in the case of localized bone loss. A high level of DBP-MAF indicates that the bone loss is likely inflammation-mediated and attributable to DBP-MAF. Treatment of the disorder with therapeutic anti-DBP-MAF antibodies is thus indicated. Sample sources for localized DBP-MAF testing include, for example, sinovial fluid from joints in the case of osteoarthritis, and gingival fluid in the case of periodontal disease. The diagnostic antibodies may also be used to measure the level of systemic DBP-MAF, such as by sampling blood plasma. A systemic increase in DBP-MAF in the case of a systemic bone loss indicates that the bone loss is likely attributable to DBP-MAF activity. Therapy with systemically-administered anti-DBP-MAF antibodies is thereby indicated.

Of course, while the therapeutic anti-DBP-MAF antibodies preferably take the form of human chimeric antibodies or other antibody types of reduced human immunogeneicity, the diagnostic anti-DBP-MAF antibodies may suitably comprise whole murine or other animal-sourced antibodies.

Generally, detection and quantification of an antigen in a specimen involves contacting the specimen with a monoclonal antibody and measuring the amount of antigen bound by the antibody, directly or indirectly by an assay means. Such assays include, for example, immunological assays such as enzyme-linked immunosorbent assay ("ELISA"), competitive enzyme-linked immunosorbent assay ("CELISA"), radioimmunoassay, fluorescent assay, radial immunodiffusion, precipitation, agglutination, and electroimmunodiffusion. The preferred antibody binding assays are those which involve attaching the anti-DBP-MAF monoclonal antibody to an insoluble support, although other assays may be employed. When the antibody is coupled to an insoluble support, the bound complex can readily be separated and detected. A wide variety of solid phase supports have been described, such as dextran, cellulose, polystyrene, polypropylene and the walls of glass tubes or slides. Plastic surfaces are adsorptive. Exposing the surface to the appropriate dilution of antibody will lead to attachment. Covalent bonding to the surface can be obtained by incorporation of cross-linking agents into the antibody surface used for coating.

The monoclonal antibodies may be detectably labeled with a label which is affixed to the antibodies. The label is detected by some physical or chemical means. Such labels include radiolabels; chromophoric labels, such as fluorescent, ultraviolet-absorbing or light absorbing labels; enzyme labels; etc. In the ELISA assay, the label is an enzyme, e.g., alkaline phosphatase, which cleaves a chromogenic substrate to release a chromophoric cleavage product. In the case of alkaline phosphatase, the presence of antigen is signalled by hydrolysis of the substrate p-nitrophenylphosphate, which releases the yellow-colored compound p-nitrophenol.

More conveniently, the label is affixed to a secondary monoclonal or polyclonal antibody or F(ab) fragment which binds the primary DBP-MAF-specific monoclonal antibody. For this double-antibody technique, the secondary antibody may advantageously comprise, for example, rabbit-, sheep-, or goat-anti-mouse IgG. The preferred assay means is an ELISA.

It must be understood that for any particular object, the specific dosage regimens should be adjusted to the individual need of the patient and the professional judgment of the person administering or supervising the administration of the therapeutic agent, either DBF-MAF or antibody against DBF-MAF. It is to be further understood that the dosages set forth herein are exemplary only and that they do not, to any extent, limit the scope or practice of the invention.

The invention is illustrated by the following non-limiting examples.

EXAMPLE 1

Bone Resorption in ia Rats Treated With Gc-MAF: Measurement of Marrow Cavity Size Mixed male and female normal and ia mutant newborn rats (Finch University of Health Sciences, The Chicago Medical School, North Chicago, Ill.) were subcutaneously injected with 200 pg human DBF-MAF (Gc-MAF) in normal saline once every four days until two weeks of age. At the end of the treatment period, the tibiae were removed from the treated and control animals, longitudinally bisected, and examined under a dissecting microscope to measure the size of the bone marrow cavity. The cavity size was expressed as a percentage of the distance between the epiphyseal plates of the tibia. The percentage of marrow cavity is a linear percentage of the shaft of the bone occupied by marrow space. The results appear in FIG. 1. The results for the treated animals are designated "GcMAF". Bars represent the mean±SEM. Bone marrow size was significantly increased in mutant rats treated with Gc-MAF, indicating enhanced osteoclast function and bone resorption.

EXAMPLE 2

Bone Resorption in ia Rats Treated With Gc-MAF: Osteoclast Morphology

Figure 2:
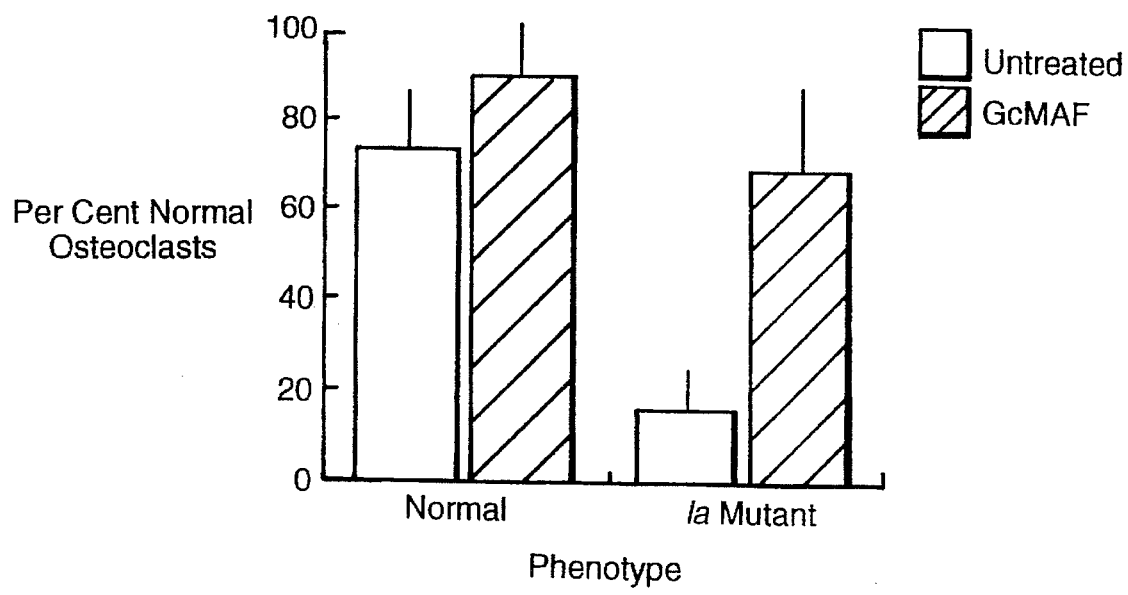
FIG. 2 indicates the number of normal osteoclasts in samples of the proximal tibiae of normal and ia mutant rats treated with GcMAF. Bars represent the mean±SEM.

Normal and ia mutant newborn rats were treated as in Example 1. At the end of the treatment period, samples of the proximal tibiae from treated and control animals were prepared for histological evaluation. Small pieces of the proximal tibia of all of the rats were fixed in 2.5% glutaraldehyde in 0.1M cacodylate buffer, pH 7.2, demineralized in 10% EDTA in 0.1M Tris buffer, pH 7.0, postfixed in 1% osmium tetroxide in 0.1M cacodylate buffer, dehydrated, and embedded in epoxy resin. Sections were cut at 1 μm and stained with toluidine blue, and the percentage of morphologically normal osteoclasts was determined at the light microscope level. More than 100 osteoclasts were evaluated from each animal. To ensure that different osteoclasts were counted, interval sections were employed, that is, 200 μm or greater intervals between sequential sections to be evaluated. The results are shown in FIG. 2 (GcMAF=drug-treated animals). Bars represent the mean±SEM. The number of mutant osteoclasts having morphological characteristics of cells actively resorbing bone was significantly increased in the Gc-MAF-treated animals.

The morphology of the tibial osteoclasts was also studied under electron microscopy. FIGS. 6A, 6B, 6C and 6D are electron micrographs of osteoclasts from proximal tibial metaphyses of untreated normal rats (6A and 6B), untreated mutant (6C) and Gc-MAF-treated mutant (6D) ia rats. The structures in the micrographs are identified as follows: O=osteoclast; V=vacuole; b=bone; n=nucleus; RB=ruffled border; cz=clear zone.

Figure 6A:
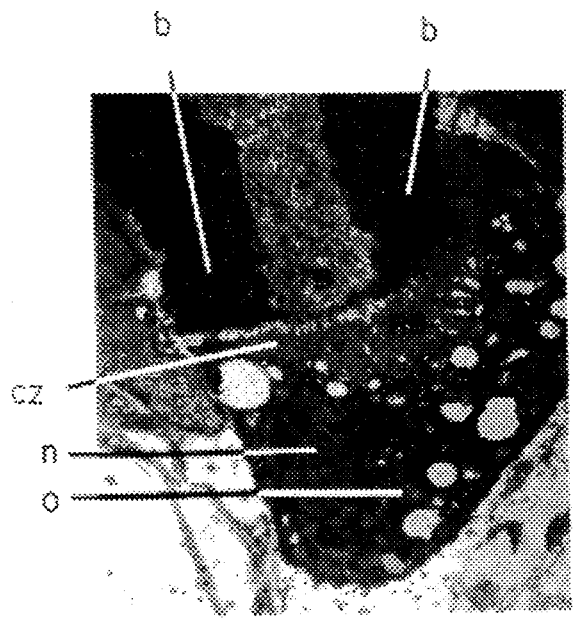
FIG. 6A is a low-power electron micrograph of an osteoclast from the proximal tibial metaphyses of untreated normal rats of ia stock. The structures in this micrograph, and in FIGS. 6B, 6C, and 6D, are identified as follows: O=osteoclast; V=vacuole; b=bone; n=nucleus; RB=ruffled border; cz=clear zone.
Figure 6B:
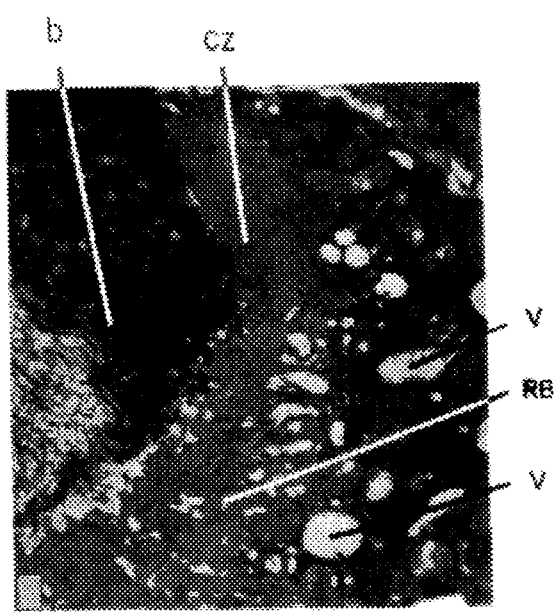
FIG. 6B is a high power photomicrograph of a portion of the osteoclast shown in FIG. 6B.

In FIG. 6A normal osteoclasts appear as multinucleated cells which attach to bone in the area of the clear zone which forms a seal around the ruffled border, the active site of bone resorption. FIG. 6B is a high power photomicrograph of a portion of the osteoclast of FIG. 6A, with greater detail of the organelle-free clear zone and the ruffled border area in which bone is being degraded. Extensive vacuolization of the cytoplasm immediately adjacent to the ruffled border is also characteristic of actively resorbing osteoclasts.

Figure 6C:
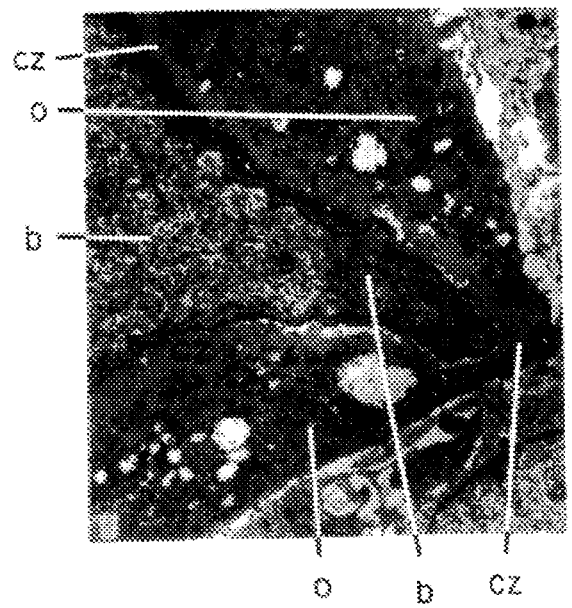
FIG. 6C is a photomicrograph of an untreated ia mutant osteoclast.

As is apparent from FIG. 6C, osteoclasts of untreated ia rats do not demonstrate ruffled borders. Clear zones are seen along much of the appositional bone surface. These ultrastructural features are indicative of inactive (non-resorbing) osteoclasts.

Figure 6D:
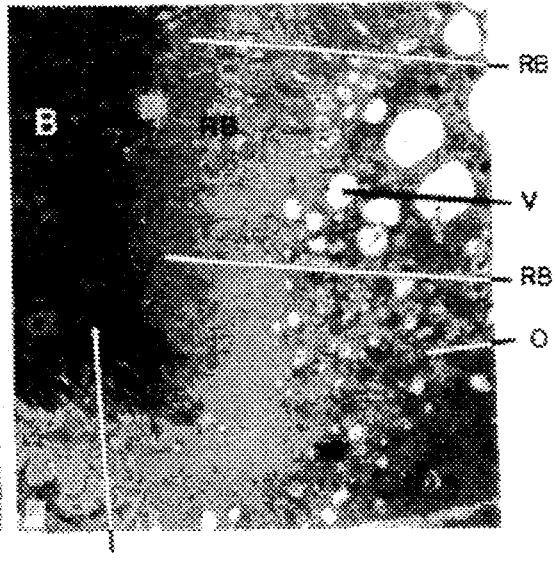
FIG. 6D is a photomicrograph of a GcMAF-treated ia mutant osteoclast.

The majority of osteoclasts in ia mutants treated with Gc-MAF demonstrated extensive ruffled border formation and cytoplasmic vacuolization as shown in the FIG. 6D photomicrograph. These cells are actively resorbing the excess skeletal matrix in the ia mutants.

EXAMPLE 3

Bone Resorption in ia Rats Treated With Gc-MAF: Osteoclast Superoxide Production (NBT-Test)

Figure 3:
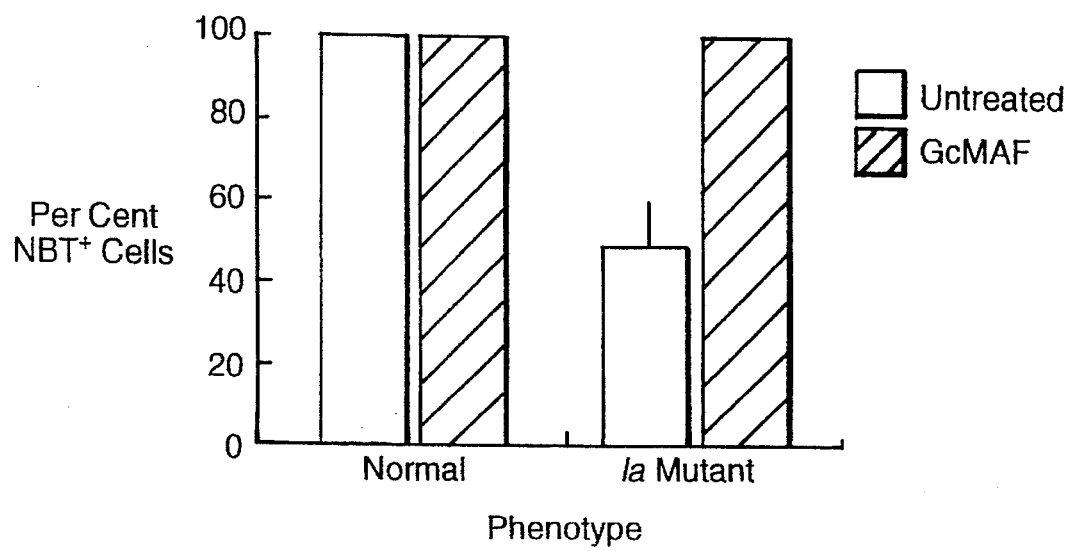
FIG. 3 shows the number of superoxide-producing cells among osteoclasts isolated from the long bones of normal and ia mutant rats following treatment with GcMAF. Bars represent the mean±SEM.

Normal and ia mutant rats were subcutaneously injected at birth with 200 pg of Gc-MAF in normal saline. Osteoclasts were isolated from long bones of treated and control animals one day later and reacted with nitroblue tetrazolium (NBT) in order to assess the cells' superoxide production. The procedure employed has been described by Ochs and Igo, *J. Pediatrics* 83: 77, 1973. Briefly, cells, after being thoroughly washed in HBSS, were suspended in RPMI 1640 culture media and incubated on endotoxin-coated glass slides for 30 minutes at 37° C. The excess culture fluid was removed, and a drop of solution containing fetal calf serum and NBT was applied to the adherent cells for 20 minutes in a moist chamber at 37° C. The slide was then washed, air-dried, fixed in methanol, and counter-stained with safranine. Slides were dried, cover-slipped, and evaluated for NBT-positive cells by the presence of blue formazan granules. The results are shown in FIG. 3 (GcMAF=drug-treated animals). Bars represent the mean±SEM. Superoxide production was increased in the GC-MAF treated mutants to a level characteristic of normal osteoclast function. Superoxide product has been shown to be correlative with active bone resorption.

EXAMPLE 4

Figure 4:
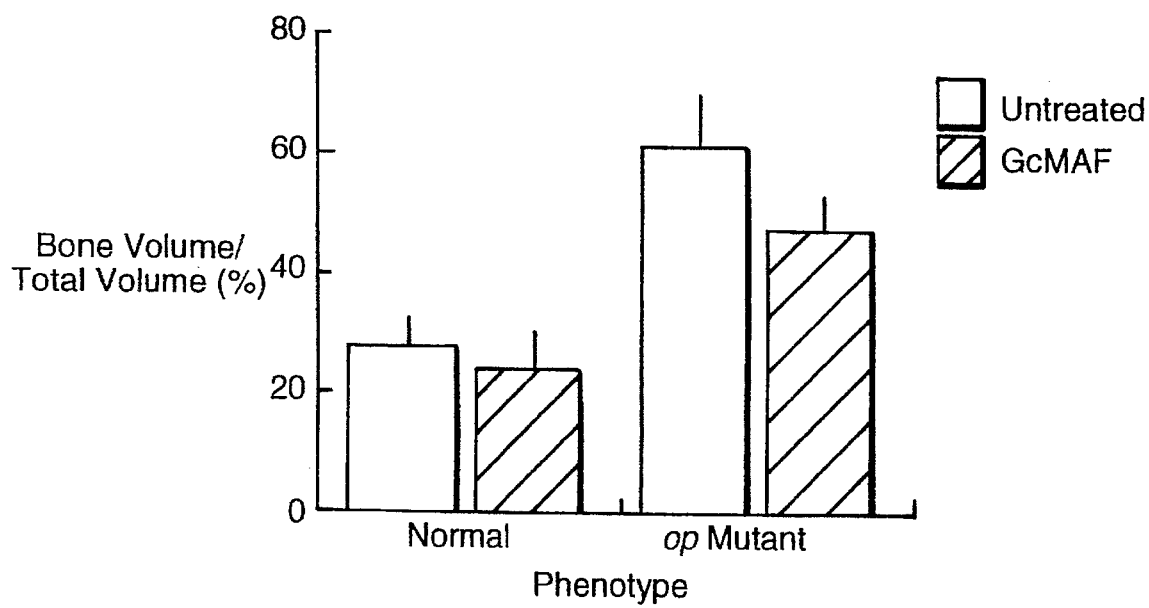
FIG. 4 provides a measure of bone volume determined from proximal tibiae samples from normal and op mutant rats treated with GcMAF. Bars represent the mean±SEM.
Figure 5:
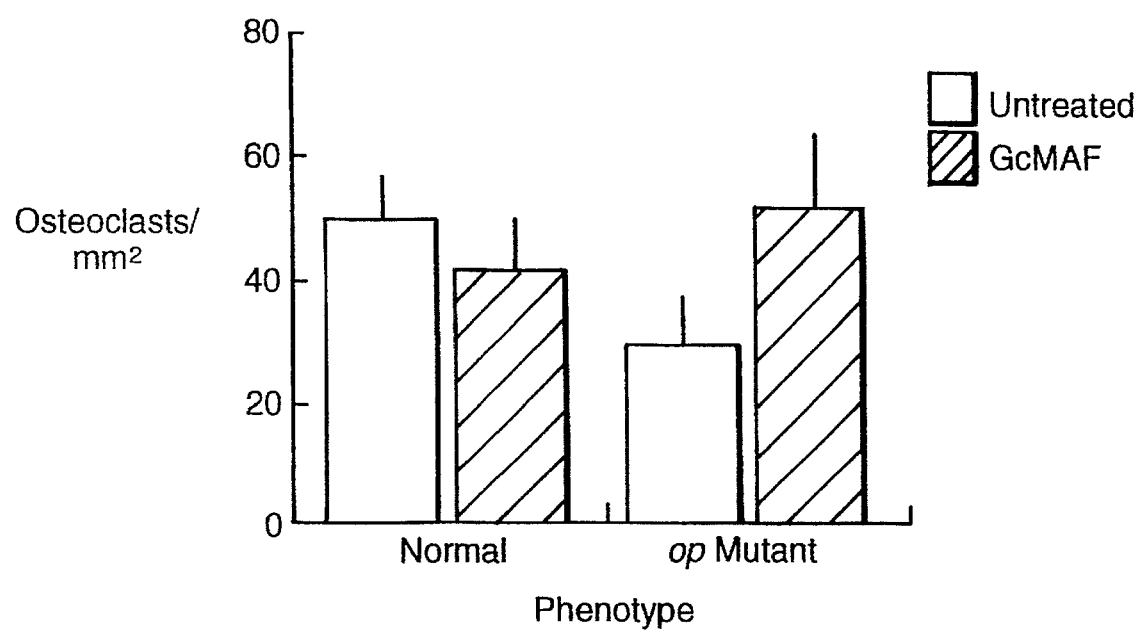
FIG. 5 indicates the number of osteoclasts found in the proximal tibiae of normal and oil mutant rats treated with GcMAF. Bars represent the mean±SEM.

Bone Resorption in op Rats Treated With Gc-MAF: Measurement of Bone Volume and Osteoclast Number Normal and op mutant rats (Temple University School of Medicine, Philadelphia, Pa.) were injected with 200 pg Gc-MAF once every 4 days until two weeks of age. At the end of the treatment period, samples of the proximal tibiae from treated and control animals were prepared for histomorphometric evaluation as follows. Proximal tibiae were fixed in 10% neutral buffered formalin, dehydrated and embedded undecalcified in K-PLAST methylmethacrylate resin. Static histomorphometric parameters of bone were measured in 4 μm thick frontal sections stained with von Kosso/tetrachrome using the OSTEOMEASURE histomorphometry system (OsteoMetrics, Inc., Atlanta, Ga.). Bone volume is shown in FIG. 4 and osteoclast number is shown in FIG. 5 (GcMAF=drug-treated animals). Bars represent the mean±SEM. Gc-MAF-treated mutants displayed a significant reduction in bone volume and an increase in the number of osteoclasts to the normal level. Light microscopic studies have indicated that approximately 75–85% of the these osteoclasts have normal osteoclast morphology.

EXAMPLE 5

Preparation of Anti-DBP-MAF Monoclonal Antibodies

The following is one typical procedure for preparing cell lines producing anti-DBF-MAF monoclonal antibodies. The procedure is essentially as described in U.S. Pat. No. 4,963,657, which provides monoclonal antibodies to the light chain of the human plasma protein factor XII.

I. Preparation of the Immunogen

DBP is obtained by either 25-hydroxy-vitamin $D_3$-SEPHAROSE® (agarose beads) affinity chromatography of retired blood according to the procedure of Link et al., *Anal. Biochem.*, 157:262, 1986, or by actin-agarose affinity chromatography according to the procedure of Haddad et al., *Biochem J.*, 218:805, 1984. DBP is then converted to DBF-MAF according to a liquid phase or immobilized enzyme procedure, such as the liquid phase and immobilized enzyme procedure of U.S. Pat. No. 5,177,002.

According to such a liquid phase enzyme procedure, about 2.6 µg DBP in 1 ml of phosphate-buffered saline containing 0.01M sodium phosphate, 0.9% NaCl and 1 mM $MgSO_4$ is treated with 2 µL of the same buffer containing 0.1 U of each of the following enzymes in combination: sialidase (e.g. Boehringer Mannheim Biochemicals, cat. No. 107590), β-galactosidase (Boehringer Mannheim, cat. No. 634395) and α-mannosidase (e.g. Boehringer Mannheim, cat. No. 107379). The enzyme-DBP mixture is incubated in microcentrifuge tubes for 30 min. at 37° C. to convert the DBP to DBP-MAF.

According to the immobilized enzyme procedure of U.S. Pat. No. 5,177,002 for converting DBP to DBF-MAF, 100 mg of CNBr-activated agarose (SEPHAROSE® 4B, agarose beads) is washed with 1 mM HCl and suspended in coupling buffer (300 µl) containing $NaHCO_3$ buffer (0.1M, pH 8.3) and NaCl (0.5M). β-Galactosidase, α-mannosidase and sialidase (2 U each enzyme) are mixed in 600 µl of the coupling buffer and incubated at room temperature for 2 hours in an end-over-end mixer. Remaining active groups in the agarose are blocked by incubation with 0.2M glycine in coupling buffer for 2 hours at room temperature. The agarose-immobilized enzyme is washed with coupling buffer to remove unabsorbed protein and glycine, followed by washing with acetate buffer (0.1M, pH 4) containing NaCl (0.5M), and additional coupling buffer. DBP protein (2.6 µg) in 1 ml of PBS-Mg (pH 5.5) is combined with a mixture of the above-prepared agarose-immobilized enzymes (2 units each enzyme) in 1 ml of PBS-Mg (pH 5.5). The reaction mixtures are incubated in 5 ml plastic tubes at 37° C. in an end-over-end mixer for 30 minutes. The reaction mixtures are thereafter spun with a table-top centrifuge at 2,000 rpm for 15 minutes. The supernatant of each reaction mixture is collected, filtered through a sterilized 0.45µ pore size filter (type HA, Millipore Company, Bedford, Mass.), and diluted.

II. Immunization

Male or female BALB/c AnSkh mice, 8–10 weeks old are immunized subcutaneously with 35 micrograms of protein/mouse in complete Freund's adjuvant (week 0) and then again subcutaneously with 35 micrograms of protein/mouse in incomplete Freund's adjuvant at week 5. Blood is removed and screened at week 7 for antibodies to the immunogen using ELISA. At week 11, 50 micrograms of immunogen/mouse in 0.15M NaCl are intraperitoneally injected. Four days later, blood is removed from the retroorbital plexus of each mouse under light anesthesia, and the strongest positive mice are selected as spleen donors. The spleens of these animals are aseptically removed and placed in tissue culture dishes (15×60 mm) containing Hank's balanced salt solution ("HBSS", Gibco, Grand Island, N.Y.) to which 50 micrograms/ml of gentamicin or "PEN/STREP" (Gibco) are added. The latter is a mixture of penicillin and streptomycin. The spleens are then transferred into other culture dishes containing HBSS. The spleens are teased apart with sterile forceps and then transferred into a centrifuge tube which is placed in ice for two minutes to allow large debris to settle. The cell suspension is transferred into another centrifuge tube and spun for ten minutes at 1200 rpm. After discarding the supernatant, the cells are resuspended in 5–10 ml of 0.17M $NH_4Cl$ (ice cold) and placed in ice for five minutes with occasional mixing in order to lyse red blood cells. The cell suspension is gently underlaid into 10 ml of a 1:1 dilution of HBSS:normal serum and centrifuged at 1200 rpm for ten minutes. Fetal calf serum ("FCS") may be used as the normal serum. The cells are then washed thrice in Dulbeco's Modified Eagle's Medium ("DME", Gibco). The number and viability of cells are then determined.

SP2/0-Agl4 myeloma cells used in the hybridization procedure are washed in the same way as the unlysed splenocytes.

III. Preparation of Splenocyte Feeder Layers

On the day of fusion, non-immune splenocytes from the same mouse strain as immunized above are processed according to the same procedure without immunization and without washing in DME. These non-immune splenocytes are used to prepare feeder layers as follows. The non-immune cells are resuspended in DME+HAT+20% FCS to a density of 2–4×106 cells/ml. These cells are seeded onto 96-well plates (1–2×105 cells/well) and incubated in 5% $CO_2$ at 35° C. overnight as a sterility check before plating out hybrid cells.

IV. Hybridization

Fusion is carried out as follows. 1.5 ml of immune splenocytes and 1.5 ml of SP2/0-Agl4 cells are piperted onto a concanavalin A-coated plate. The cell concentration of each cell type is adjusted so that the ratio of splenocytes to SP2/0-Agl4 cells is 2–3:1, with a total of 7–10×10$^7$ cells/plate. The plates are then incubated in 5% $CO_2$ at 37° C. for 45–60 minutes to allow for attachment of the cells to concanavalin A. Fusion is performed by adding 1 ml of a 50% DME:PEG solution to each plate, drop by drop. The plates are left standing for 15 seconds after the addition of the first drop. The cells are then washed twice with 5 ml of DME. Following addition of 5 ml of DME+20% FCS/plate, the cells are incubated overnight.

V. Selection and Growth of Hybridomas

Following overnight incubation, the cells from the above hybridization procedure are transferred into centrifuge tubes and spun at 1500 rpm for 15 minutes. The supernatants are discarded. The cells from each tube are suspended in 40–45 ml of DME+HAT+20% FCS and transferred into the 96-well plates (0.1 ml cell suspension/well) containing non-immune sptenocyte feeder layers as prepared in "III. Preparation of Splenocyte Feeder Layers", above. The plates are cultured with 10% $CO_2$ at 37° C. in a humid atmosphere. The cells were allowed to grow for 3–5 days, after which an additional 0.1 ml of DME+HAT+20% FCS are added to each well.

Hybrids are checked daily. Three to four weeks after fusion, the cells are switched to DME+HAT+10% FCS (no aminopterin). Hybridoma cultures with antibody reactive to the immunogen are selected, and cloned and subcloned by a limiting dilution technique (McKearn, T. J., "Cloning of Hybridoma Cells by Limiting Dilution and Fluid Phase" in *Monoclonal Antibodies*, p. 347). Cells from the strongest antigen-position subcloned cultures as determined by ELISA screening are selected and injected intraperitoneally (about $2 \times 10^6$ cells in 0.5 ml PBS/mouse) into BALB/c mice which have been primed 10–14 days previously with 0.5 ml of pristane (2,6,10,14-tetramethylpentadecane). After 7–14 days, the blood is removed from the retro-orbital plexus of each mouse, under light ether anesthesia, and the tumor-induced ascites fluid is harvested.

VI. Purification of the Monoclonal Antibodies

Antibody from ascites fluid prepared above may be purified by Protein-A affinity chromatography using a commercially available kit (AFFI-GEL Protein-A, BioRad Corp., Richmond, Calif.). Ascites fluid is diluted 1:1 in a binding buffer. The crude material is applied onto the protein-A column, and the column is washed with binding buffer such that the absorbance at 280 nm is less than 0.025. The antibody is then eluted with an acidic buffer. The peak of elution is pH neutralized, pooled, concentrated and dialyzed against 0.02M Tris, 0.15M NaCl, 0.03% sodium azide, pH 7.5. The concentration of the antibody is determined by reading the absorbance at 280 nm and calculating the mg/ml by using a 1% extinction coefficient of 14.2. The final antibody concentration is in the range of 2–5 mg/ml. Concentrations of the monoclonal antibodies may be converted from mg/ml to micromolar using an antibody molecular weight of 150 kDa.

VII. Screening Method for Antibody Inhibition of Bone Resorption

The monoclonal antibodies as prepared above are readily screened for their ability to inhibit osteoclast bone resorption using either synthetic (ceramic thin film method of Davies et al., *Cells and Materials* 3(30), 245–256, 1993) or natural (bone or dentine: Chambers et al., *J. Cell Sci.* 66:383–399, 1984; Boyde et al., *Br. Dent. J.* 156:216–220, 1984) substrates. Osteoclasts are isolated from the long bones of newborn rat or rabbit pups (Chambers and Dunn, *J. Pathol.* 137:193–203, 1982). These cells are seeded onto the appropriate synthetic or natural substrate and allowed to adhere and resorb bone for a period of time ranging from 24 to 72 hours. Visualization and quantitation of the creation of resorption lacunae during culture is straightforward using various techniques, including light microscopy, image analysis, SEM or confocal SEM.

A. Preparation of Osteoclast Cultures

Femurs and tibiae are removed from newborn rabbits or rats. The long bones are rinsed several times in supplemented M199(E) medium. This medium contains 0.7 g/l sodium bicarbonate 6.5 g/l Hepes, 100 IU/ml penicillin-streptomycin and 10% fetal calf serum, at a pH of 6.8. The epiphyseal ends of the bones are cut off (discarded) and the bone is split longitudinally. The split bones are curetted using a scalpel and the bone fragments are agitated using a wide-mouth pipette. The larger fragments are allowed to settle for 5–10 seconds and the remaining suspension is aspirated and transferred to a microtube and spun down to concentrate the cells. The loose pellet of cells is resuspended in a small volume (500 µl) and cells are seeded onto an appropriate substrate, e.g., slices of ground, cortical bone or dentine (natural substrate), or commercially available synthetic (OSTEOLOGIC, Millienium Biologix Inc., Kingston, Ont.) disks. Small volumes of the cell suspensions are layered over the substrate and incubated at 37° C. in 5% $CO_2$ and air for 30 minutes to allow osteoclasts to attach. The substrate is then removed from the well, rinsed gently and put back into experimental and control wells. Specific concentrations of DBP-MAF (ranging from 10–10,000 pg/ml) in supplemented M199 medium are added to the control and experimental wells. Some of the experimental wells further receive specific concentrations of candidate anti-DBP-MAF monoclonal antibody in the same range, equal to the amount of DBP-MAF added to the same well. The cultures are incubated for a period of 24 to 72 hours, and bone resorption is assessed.

B. Evaluation of Bone Resorption

Bone resorptrion is assessed by counting the number of resorption pits under a light microscope (Murrills and Dempster, *Bone*, 11, 333–344 (1990)); by quantitating the area occupied by the resorption pits by image analysis (Davis et al., *Cells and Materials*, 3, 245–256 (1993); or by quantitating the area or volume of resorption by scanning electron microscopy (Chambers et al., *J. Cell Sci.* 70, 61–71 (1984); Boyde et al., *Scanning Electron Microscopy*, III, 1239–1271, (1985)).

All references cited herein with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method of promoting osteoclast bone resorption, comprising the step of:

administering to an individual in need of such treatment an effective amount of activated vitamin D-binding factor.

2. A method of treating osteopetrosis, comprising the step of:

administering to an individual in need of such treatment an effective amount of activated vitamin D-binding factor.

3. A method according to claim 2 wherein the activated vitamin D-binding factor consists of human activated vitamin D-binding factor.

4. A method according to claim 2 wherein the activated vitamin D-binding factor consists of non-human mammalian activated vitamin D-binding factor.

5. A method according to claim 2 wherein said step of administering is by local delivery of the activated vitamin D-binding factor.

6. The method of claim 1 wherein the individual in need of such treatment has B cells which are deficient in lysophosphatidylcholine-inducible β-galactosidase activity.

7. The method of claim 1 wherein the individual in need of such treatment is deficient in serum DBP or DBP-MAF.

8. The method of claim 1 wherein macrophage number of the individual in need of such treatment fails to increase upon treatment with lyso-phosphatidylcholine.

9. The method of claim 1 wherein superoxide production in the individual in need of such treatment fails to increase upon treatment with lysophosphatidylcholine.

10. The method of claim 2 wherein the individual in need of such treatment has B cells which are deficient in lysophosphatidylcholine-inducible β-galactosidase activity.

11. The method of claim 2 wherein the individual in need of such treatment is deficient in serum DBP.

12. The method of claim 2 wherein macrophage number of the individual in need of such treatment fails to increase upon treatment with lysophosphatidylcholine.

13. The method of claim 2 wherein superoxide production of the individual in need of such treatment fails to increase upon treatment with lysophosphatidylcholine.

14. The method of claim 2 wherein the individual in need of such treatment is deficient in serum DBP-MAF.

15. The method according to claim 2 wherein said osteopetrosis is congenital osteopetrosis.

* * * * *